(12) United States Patent
Blankenship et al.

(10) Patent No.: US 6,878,329 B2
(45) Date of Patent: Apr. 12, 2005

(54) METHOD OF MAKING A CATHETER BALLOON USING A POLYIMIDE COVERED MANDREL

(75) Inventors: Delma M. Blankenship, Sunnyvale, CA (US); Jeong S. Lee, Diamond Bar, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 227 days.

(21) Appl. No.: 10/208,531

(22) Filed: Jul. 30, 2002

(65) Prior Publication Data

US 2004/0020586 A1 Feb. 5, 2004

(51) Int. Cl.[7] ............ B29C 53/60; B29C 53/56; B29C 53/82
(52) U.S. Cl. ............ 264/294; 264/285; 264/295; 264/320; 264/339; 156/189; 156/195; 156/425; 425/403
(58) Field of Search ............ 264/285, 294, 264/295, 320, 339; 156/189, 195, 425; 425/403

(56) References Cited

U.S. PATENT DOCUMENTS

| | | | |
|---|---|---|---|
| 2,941,911 A | * | 6/1960 | Kumnick et al. ............ 156/86 |
| 3,879,516 A | | 4/1975 | Wolvek ............ 264/135 |
| 4,155,970 A | * | 5/1979 | Cassell ............ 264/137 |
| 4,478,898 A | * | 10/1984 | Kato ............ 428/36.91 |
| 4,659,622 A | | 4/1987 | Barta et al. ............ 428/379 |
| 4,791,966 A | * | 12/1988 | Eilentropp ............ 138/154 |
| 4,826,706 A | | 5/1989 | Hilker et al. ............ 427/120 |
| 5,630,806 A | * | 5/1997 | Inagaki et al. ............ 604/524 |
| 5,718,973 A | | 2/1998 | Lewis et al. ............ 623/1.32 |
| 5,752,934 A | | 5/1998 | Campbell et al. |
| 5,868,704 A | | 2/1999 | Campbell et al. ...... 604/103.11 |
| 5,913,871 A | * | 6/1999 | Werneth et al. ............ 623/1.11 |
| 5,951,539 A | | 9/1999 | Nita et al. ............ 604/526 |
| 6,016,848 A | | 1/2000 | Egres, Jr. ............ 138/137 |
| 6,120,477 A | | 9/2000 | Campbell et al. ........ 604/96.01 |

FOREIGN PATENT DOCUMENTS

| | | |
|---|---|---|
| EP | 0421650 A1 | 4/1991 |
| EP | 1068876 A2 | 1/2001 |
| WO | WO 91/13648 A1 | 9/1991 |
| WO | WO 95/05555 | 2/1995 |
| WO | WO 97/02791 | 1/1997 |
| WO | WO 02/11806 A1 | 2/2002 |

OTHER PUBLICATIONS

Phelps Dodge brochure, *A Primer on Polyimide Tubing*, pp. 1.

U.S. patent application Publication No. 2002/0082637 A1; Published Jun. 27, 2002; Rommel C. Lumauig; Entitled: "Catheter And Method For Making The Same".

* cited by examiner

*Primary Examiner*—Michael Colaianni
*Assistant Examiner*—Michael I Poe
(74) *Attorney, Agent, or Firm*—Fulwider Patton Lee & Utecht, LLP

(57) ABSTRACT

A method of making a catheter balloon or other tubular medical device or component, in which a sheet of polymeric material is wrapped on a mandrel and heated to fuse sections of the wrapped sheet together to form a tube. The mandrel has a metallic core and a jacket on an outer surface of the metallic core, and the wrapped sheet of polymeric material is heated without corroding the metallic core of the mandrel. In a presently preferred embodiment, the sheet is formed of a fluoropolymeric material, and the resulting fluoropolymeric tube forms at least a layer of a catheter balloon.

17 Claims, 2 Drawing Sheets

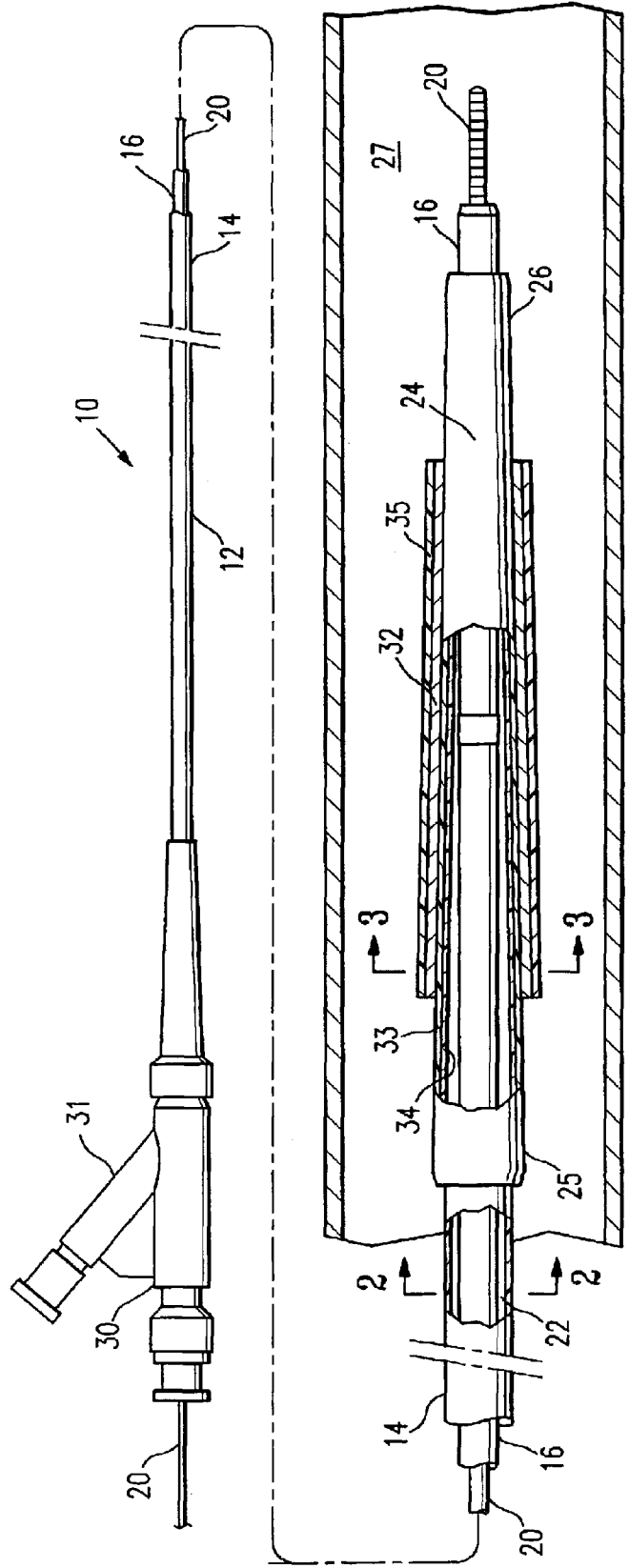
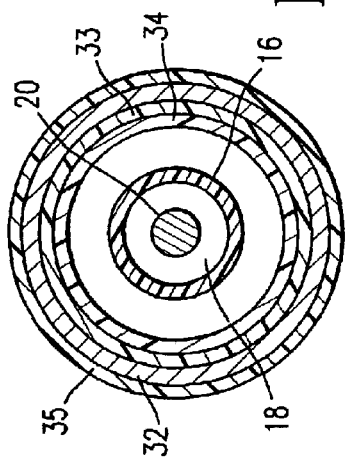
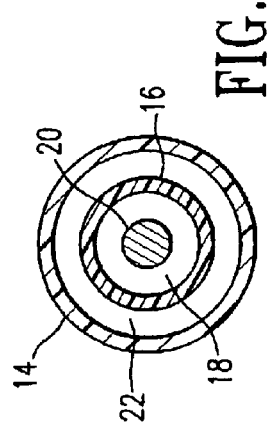
FIG. 1
FIG. 2
FIG. 3

METHOD OF MAKING A CATHETER BALLOON USING A POLYIMIDE COVERED MANDREL

BACKGROUND OF THE INVENTION

This invention generally relates to medical devices, and particularly to intracorporeal devices for therapeutic or diagnostic uses such as balloon catheters, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e., reformation of the arterial blockage, which necessitates either another angioplasty procedure or some other method of repairing or strengthening the dilated area. To reduce the restenosis rate and strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to an angioplasty balloon catheter, and expanded to a larger diameter by expansion of the balloon. The balloon is deflated to remove the catheter and the stent left in place within the artery at the site of the dilated lesion. Stent covers commonly provided on an inner or an outer surface of the stent have been used in, for example, the treatment of pseudo-aneurysms and perforated arteries and to prevent prolapse of plaque, and generally comprise a cylindrical tube of synthetic or natural material. Similarly, vascular grafts comprising cylindrical tubes commonly made from tissue or synthetic materials such as polyester, expanded polytetrafluoroethylene, and DACRON, are configured to be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which instead readily expand to the working diameter within the patient's body lumen from a generally cylindrical or tubular shape (i.e., essentially no wings) that conforms to the catheter shaft.

Catheter balloons formed of expanded polytetrafluoroethylene (ePTFE) expanded in place within the patient's body lumen without blow molding the ePTFE tubing have been disclosed. Prior disclosed methods of forming the ePTFE balloon involve wrapping a sheet of ePTFE on a mandrel and then heating the wrapped sheet to fuse the layers of wrapped material together. One difficulty has been removing the resulting ePTFE tube from the mandrel after the layers of wrapped material are fused together without damaging the ePTFE tube.

SUMMARY OF THE INVENTION

This invention is directed to a method of making a catheter balloon or other tubular medical device or component thereof, in which a sheet of polymeric material is wrapped on a mandrel and heated to fuse sections of the wrapped sheet together, to form a polymeric tube. The mandrel has a metallic core and a jacket on an outer surface of the metallic core, and the wrapped sheet of polymeric material is heated without corroding the metallic core of the mandrel. In a presently preferred embodiment, the sheet is formed of a fluoropolymeric material, and the resulting fluoropolymeric tube forms at least a layer of a catheter balloon.

The mandrel jacket prevents or inhibits corrosion of the metallic core of the mandrel during the formation of the fluoropolymeric tube. Corrosive species are produced by the fluoropolymeric material during high temperature heating thereof, thus resulting in a highly corrosive environment at the high temperatures used to fuse sections of the wrapped sheet together. The mandrel jacket protects the metallic core of the mandrel from the highly corrosive environment which would otherwise corrode metals such as stainless steel or carbon steel used to form the metallic core of the mandrel. The corrosion typically includes affects such as oxidation, discoloration, flaking and loss of mechanical properties. Such corrosion makes it difficult to remove the fluoropolymeric tube from the mandrel without damaging the fluoropolymeric tube, and requires frequent disposal of the mandrel.

The polymeric material forming the jacket is dimensionally stable at the elevated temperatures used during formation of the fluoropolymeric tube, and specifically during high temperature fusion (i.e., thermal) bonding of the wrapped sheet of fluoropolymeric material to form a fluoropolymeric tube. Thus, the dimensions of the jacket do not change significantly during the heating of the wrapped fluoropolymeric material. Preferably, the outer diameter and length of the jacket are substantially unchanged (i.e., a change of about 0% to about 10%) during the heating of the fluoropolymeric material to form the fluoropolymeric tube. The inner diameter of the resulting fluoropolymeric tube is determined by the outer diameter of the mandrel jacket. Consequently, the dimensionally stable jacket facilitates production of a fluoropolymeric tube having a desired inner diameter.

The polymeric material forming the jacket is preferably a high temperature material having a glass transition temperature (Tg) of about 350° C. to about 450° C., and most preferably about 390° C. to about 420° C. The jacket thus has excellent dimensional stability at the processing temperature of the fluoropolymeric material. In one embodiment, the polymeric material forming the jacket is selected from the group consisting of thermoset polyimide, and a thermoplastic polyimide. The polyimide materials have relatively high glass transition temperatures. Additionally, the polyimide materials have a high abrasion resistance and a high modulus which are maintained at elevated temperature. In a presently preferred embodiment, the jacket comprises a thermoset polyimide, due to the high glass transition temperature of the thermoset polyimide. The thermoset polyimide has a very high glass transition temperature of approximately 390° C. to about 420° C., more specifically about 400° C. to about 410° C. (as measured by differential scanning calorimetry (DSC). Additionally, the thermoset polyimide has excellent dimensional stability at the fluoropolymer fusing temperature of about 370° C. for the duration of the heat treatment, e.g., about 20 to about 30 minutes. Specifically, the thermoset polyimide is crosslinked, and thus has high dimensional stability at or near the glass transition temperature of the polyimide. As a result, the polyimide tube maintains thin-walled, controlled dimensions during formation of the fluoropolymeric tube. Thermoplastic polyimide, such as Aurum available from Mitsui Toatsu Chemical, Inc., which has a Tg of about 230° C. to about 270° C., may also be used, but is less preferred than the more highly dimensionally stable thermoset polyimide. Thus, the mandrel jacket material has high dimensional stability, and specifically has a glass transition temperature above the processing temperature of the fluoropolymeric material, unlike polymeric materials such as polytetrafluoroethylene and silicone.

In a presently preferred embodiment, the sheet of fluoropolymeric material comprises a polymer having a porous structure, which in one embodiment is expanded polytetrafluoroethylene (ePTFE). In one embodiment, the porous material has a node and fibril microstructure. ePTFE typically has a node and fibril microstructure, and is not melt extrudable. The node and fibril microstructure, when present, is produced in the material using conventional methods, and the sheet of polymeric material preferably has the desired microstructure (e.g., porous and/or node and fibril) before being wrapped on the mandrel. In one presently preferred embodiment, the polymeric material cannot be formed into a balloon by conventional balloon blow molding, and is instead formed into a balloon by bonding wrapped layers of the polymeric material together to form a tubular member, and preferably provided with a nonporous second layer or liner, to form an inflatable balloon.

In a presently preferred embodiment, the tubular medical device or medical device tubular component is an inflatable balloon for a catheter. A balloon formed according to the method of the invention can be used on a variety of suitable balloon catheters including coronary and peripheral dilatation catheters, stent delivery catheters, drug delivery catheters and the like. Although discussed below primarily in terms of the embodiment in which the medical device tubular component is an inflatable member such as a balloon for a catheter, it should be understood that other expandable medical devices and components are included within the scope of the invention including stent covers and vascular grafts.

The method of the invention prevents or inhibits corrosion of the metallic core of the mandrel used in forming a polymeric tubular medical device or component. Moreover, the method facilitates removal of the resulting polymeric tube from the mandrel without damaging the polymeric tube, and provides a tube having a desired inner diameter. These and other advantages of the invention will become more apparent from the following detailed description and accompanying exemplary figures.

BRIEF DESCRIPTION OF THE DRAWINGS

FIG. 1 is an elevational view, partially in section, of a stent delivery balloon catheter embodying features of the invention.

FIG. 2 is a transverse cross sectional view of the balloon catheter shown in FIG. 1, taken along line 2—2.

FIG. 3 is a transverse cross sectional view of the balloon catheter shown in FIG. 1, taken along line 3—3.

DETAILED DESCRIPTION OF THE INVENTION

Figure 6:
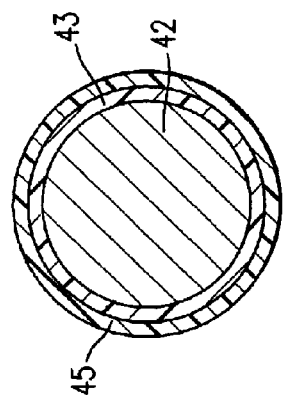
FIG. 6 is a transverse cross sectional view of the assembly shown in FIG. 5, taken along line 6—6.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best illustrated in FIG. 2 showing a transverse cross sectional view of the distal end of the catheter shown in FIG. 1, taken along line 2—2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that its interior is in fluid communication with inflation lumen 22. An adapter 30 at the proximal end of catheter shaft 12 is configured to provide access to guidewire lumen 18, and to direct inflation fluid through arm 31 into inflation lumen 22. FIG. 1 illustrates the balloon 24 prior to complete inflation, with an expandable stent 32, having a tubular cover 35 thereon, mounted on a working length of the balloon 24. The distal end of catheter may be advanced to a desired region of a patient's body lumen 27 in a conventional manner, and balloon 24 inflated to expand the covered stent 32, and the balloon deflated, leaving covered stent 32 implanted in the body lumen 27. FIG. 3 illustrates a transverse cross sectional view of the catheter shown in FIG. 1, taken along line 3—3.

In the embodiment illustrated in FIG. 1, balloon 24 has a first layer 33 and a second layer 34. In a presently preferred embodiment, the balloon 24 first layer 33 comprises a fluoropolymeric material, which is in one embodiment is a porous fluoropolymeric material, and preferably a microporous fluoropolymeric material having a node and fibril microstructure, such as ePTFE. In the embodiment illustrated in FIG. 1, first layer 33 is formed of ePTFE, and the second layer 34 is formed of a polymeric material preferably different from the polymeric material of the first layer 33. Although discussed below in terms of one embodiment in which the first layer 33 is formed of ePTFE, it should be understood that in other embodiments the first layer may comprise other materials. The second layer 34 is preferably formed of an elastomeric material, including polyurethane elastomers, silicone rubbers, styrene-butadiene-styrene block copolymers, polyamide block copolymers, and the like. In a preferred embodiment, layer 34 is an inner layer relative to layer 33, although in other embodiments it may be an outer layer. Layer 34 formed of an elastomeric material limits or prevents leakage of inflation fluid through the microporous ePTFE to allow for inflation of the balloon 24, and expands elastically to facilitate deflation of the balloon 24 to a low profile deflated configuration. The elastomeric material forming layer 34 may consist of a separate layer which neither fills the pores nor disturbs the node and fibril structure of the ePTFE layer 33, or it may at least partially fill the pores of the ePTFE layer 33.

Figure 4:
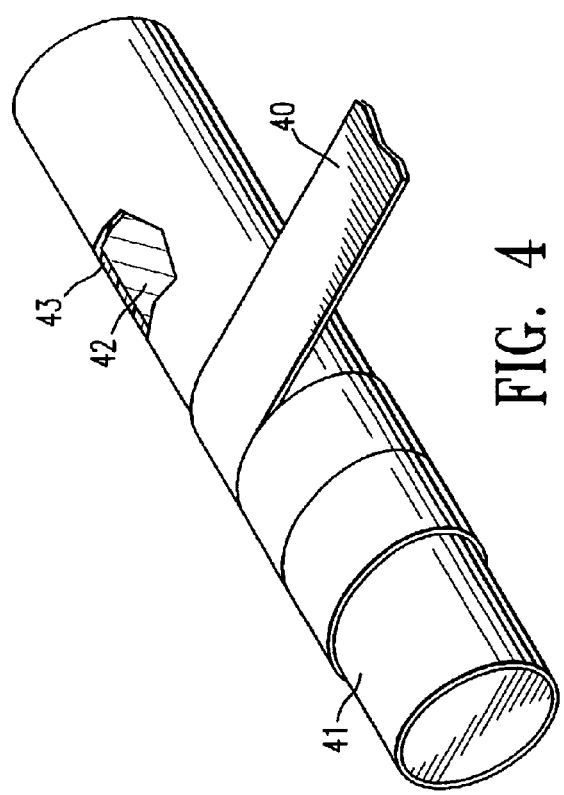
FIG. 4 illustrates an assembly of a sheet of polymeric material on a mandrel, partially in section, during wrapping of the polymeric sheet on the mandrel to form a layer of the balloon of FIG. 1, in a method which embodies features of the invention.

FIG. 4 illustrates the formation of fluoropolymeric layer 33 of the balloon 24 of FIG. 1, in a method which embodies features of the invention. In FIG. 4, a sheet 40 of fluoropolymeric material is being wrapped on a mandrel 41 having a metallic core 42 and a jacket 43 on an outer surface of the core 42. The jacket 43 covers the metallic core of 42 of the mandrel. Thus, during heating of the wrapped sheet 40 to fuse sections of the wrapped sheet together to form a fluoropolymeric tube, the metallic core 42 of the mandrel 41 is covered by the jacket 43. The exposed ends of the core 42 which are not covered by the jacket 43 typically do not result in significant corrosion of the core, at least in part because of the small surface area of the exposed ends.

In a presently preferred embodiment, the polymeric material of the mandrel jacket 43 is a thermoset polymeric material such as a thermoset polyimide such as Kapton available from DuPont Chemical Company, or available from Phelps Dodge High Performance Conductors. Tubing forming the thermoset polyimide jacket 43 is typically formed by a solution process, such as by dip coating a rod and removing the rod, to thereby produce a polyimide tubular member having a lumen configured for receiving the metallic core 42 of the mandrel 41 therein. In a suitable solution forming process, a polyimide solution is dip, or otherwise, coated onto a neckable rod, as described in U.S. Pat. Nos. 4,826,706 and 4,659,622, and the Manufacturing Process section of the Phelps Dodge High Performance Conductors brochure, A Primer on Polyimide Tubing, pp. 1, incorporated herein by reference in their entireties, and then separated intact from the rod, to thereby produce the polyimide tubular member. The dip coated rod can be passed through dies to control the outer dimension of the polyimide jacket 43, and the diameter of the removable rod determines the inner diameter of the polyimide jacket 43.

Figure 5:
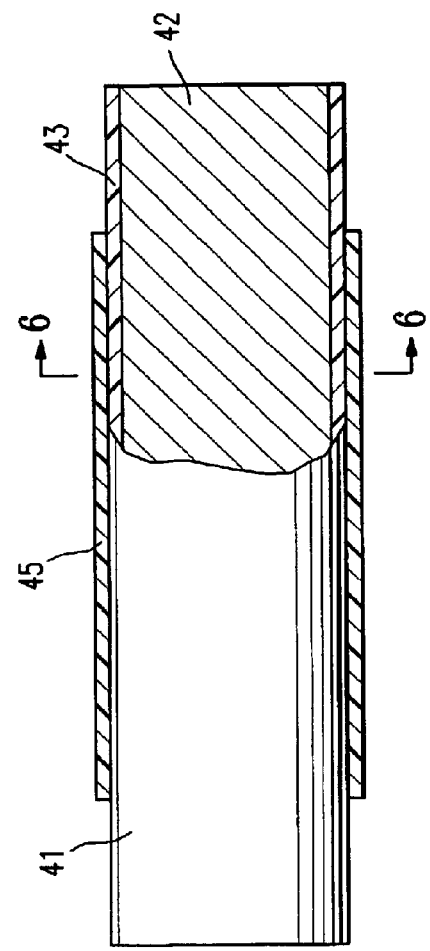
FIG. 5 is a longitudinal cross sectional view of the assembly of FIG. 4 after the polymeric sheet is wrapped on the mandrel and heat fused to form a tube, before the polymeric tube is removed from the mandrel.

The mandrel jacket 43 has a wall thickness which is sufficiently large to provide a dimensionally stable jacket 43, and sufficiently small to facilitate necking or otherwise stressing the jacket 43 during removal of the jacket 43 from inside the fluoropolymeric tube 45 (FIG. 5). The wall thickness of the mandrel jacket 43 is typically about 0.025 to about 0.15 mm, and more preferably about 0.05 to about 0.1 mm. In one embodiment, the mandrel jacket 43 has a length about equal to the length of the metallic core 42. In another embodiment the jacket has a length shorter than the length of the core, to enhance the grip of the wrapped sheet 40 onto the mandrel 41. The mandrel jacket 43 has a length of about 9 to about 11 cm, for a metallic core 42 having a length of about 9.5 to about 12 cm (which includes within that length about 2 cm which is for grabbing by the winding machine and which is therefore not available for having the fluoropolymeric sheet 40 wrapped thereon). The mandrel jacket 43 has an outer diameter of about 0.15 to about 1 cm, more preferably about 0.2 to about 0.5 cm before being placed on the mandrel core 42. The mandrel core 42 typically has an outer diameter, less than the diameter of the jacket, of about 0.15 to about 1 cm, more preferably about 0.2 to about 0.5 cm (and for example about 0.2 mm less than the inner diameter of the jacket to facilitate being placed therein).

In the embodiment of FIG. 4, the sheet 40 is a long strip of fluoropolymeric material having longitudinal edges along the length of the strip which are longer than the width of the sheet 40, and the sheet 40 is spirally wrapped around mandrel 41 to form a tube. The sheet 40 is wrapped on the mandrel 41 so that the longitudinal edges of the sheet 40 are brought together in an abutting or overlapping relation. The sheet 40 of fluoropolymeric material is preferably wrapped along a length of the mandrel 41 to form one or more layers of wrapped material. In one embodiment, multiple layers of fluoropolymeric material are wrapped on the mandrel, by for example, wrapping the sheet 40 down the length of the mandrel 41 to form a first layer and then back again over the first layer one or more times to form additional layers, which in one embodiment results in two to about five layers, preferably about three to about four layers of material together forming the fluoropolymeric layer 33. In the embodiment having multiple layers of fluoropolymeric material, the multiple layers are typically fused together during the heat fusion of the abutting or overlapping edges of the wrapped sheet 40 to form the fluoropolymeric tube.

FIG. 5 illustrates a longitudinal cross section of the assembly shown in FIG. 4, after the wrapping of the sheet 40 is completed and the fluoropolymeric material is heated, for example in an oven, to heat fuse the wrapped sheet 40 together to form a fluoropolymeric tube 45. FIG. 6 illustrates a transverse cross section of the assembly of FIG. 5, taken along line 6—6. In the embodiment in which the polymeric material of sheet 40 is ePTFE, the elevated temperature is sufficient to soften the ePTFE, and is preferably at or above the sintering temperature of the ePTFE, and is more specifically about 350° C. to about 390° C. The ePTFE wrapped sheet 40 is preferably heated for about 10 to about 30 min. Due to the dimensional stability of the polymeric material forming jacket 43 at the elevated temperature used to fuse the wrapped fluoropolymeric sheet 40, the dimensions of the jacket 43 preferably do not change, i.e., increase or decrease, as a result of the heat fusion.

The assembly illustrated in FIG. 5 is allowed to cool, and the resulting fluoropolymeric tube 45 is removed from the jacketed mandrel 41. Specifically, the assembly is typically placed in a loosener fixture or otherwise worked to loosen the fluoropolymeric tube 45 from the jacketed mandrel 41. The core 42 with the jacket 43 thereon are then removed together from the tube 45 lumen, or alternatively, the jacket 43 and fluoropolymeric tube 45 thereon may be removed together from the core 42 and the jacket 43 then removed from inside the fluoropolymeric tube 45 (with the metallic core 42 of the mandrel 41 already removed therefrom). The metallic core 42 of the mandrel 41 is protected from corrosion by the jacket 43, so that the core 42 can be reused. The jacket 43 is typically reused several times before being replaced by a new jacket in the event of degradation of the jacket 43.

The fluoropolymeric tube 45 is typically further processed to complete the formation of layer 33, and is bonded to or otherwise combined with layer 34 to complete formation of the balloon 24. For example, the fluoropolymeric tube 45 is preferably further processed by being stretched, sintered, compacted, and then sintered again, to provide the desired properties such as the desired dimension, and dimensional stability (i.e., to minimize changes in length occurring during inflation of the balloon).

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), more specifically about 0.037 inch (0.094 cm), and a wall thickness of about 0.002 to about 0.008 inch (0.0051 to 0.02 cm), more specifically about 0.003 to 0.005 inch (0.0076 to 0.013 cm). The inner tubular member 16 typically has an inner diameter of about 0.01 to about 0.018 inch (0.025 to 0.046 cm), more specifically about 0.015 to about 0.016 inch (0.038 to 0.04 cm), and a wall thickness of 0.002 to 0.005 inch (0.005 to 0.013 cm). The overall working length of the catheter 10 may range from about 100 to about 150 cm, and is typically about 143 cm. The balloon 24 typically has a length of about 0.5 cm to about 6 cm, and an inflated working diameter of about 2 to about 10 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives.

Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire stent delivery catheter, the catheter may comprise other types of intravascular catheters, such as rapid exchange dilatation catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter.

While the present invention is described herein in terms of certain preferred embodiments, those skilled in the art will recognize that various modifications and improvements may be made to the invention without departing from the scope thereof. For example, although the sheet 40 is spirally wrapped on mandrel 41 as illustrated in FIG. 4, the polymeric material forming the tube 45 may be applied to the mandrel 41 in a variety of suitable configurations including folding around the mandrel with a longitudinally oriented seam along the length of the mandrel. Similarly, although discussed in terms of use in a method of heat fusing wrapped material together to form a tube, the dimensionally stable, corrosion resistant jacketed mandrel of the invention may be used in a variety of heat treatments including heat stabilization of a polymeric member thereon. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A method of making a tubular medical device or component formed of a fluoropolymeric material, comprising:
    a) wrapping a sheet of a fluoropolymeric material on a mandrel, the mandrel having a metallic core and a jacket of a polyimide material on an outer surface of the metallic core;
    b) heating the wrapped sheet of fluoropolymeric material on the mandrel to fuse sections of the wrapped sheet together to form a fluoropolymeric tube; and
    c) removing the fluoropolymeric tube from the metallic core and the jacket of the mandrel.

2. The method of claim 1 wherein b) comprises heating the wrapped sheet without corroding the metallic core of the mandrel.

3. The method of claim 1 wherein the fluoropolymeric material of the sheet is expanded polytetrafluoroethylene, and the sheet is spirally wrapped on the mandrel.

4. The method of claim 1 wherein the metallic core of the mandrel is stainless steel, and b) comprises heating the wrapped sheet in an oven.

5. The method of claim 1 wherein c) comprises removing the polyimide jacket and the metallic core of the mandrel together from inside the fluoropolymeric tube.

6. The method of claim 1 wherein c) comprises removing the metallic core of the mandrel from inside the fluoropolymeric tube and removing the polyimide jacket from inside the fluoropolymeric tube after the metallic core of the mandrel is removed therefrom.

7. The method of claim 1 wherein the medical device component is a catheter balloon and including, after c) securing a liner to the fluoropolymeric tube to form the catheter balloon.

8. The method of claim 1 wherein the polyimide jacket is a thermoset polyimide having an outer diameter and a length, and b) comprises heating the wrapped sheet at about 350° C. to about 390° C. for about 10 minutes to about 30 minutes.

9. The method of claim 8 wherein the thermoset polyimide jacket outer diameter before b) is substantially unchanged after b).

10. The method of claim 8 wherein the thermoset polyimide jacket length before b) is substantially unchanged after b).

11. A method of making at least a layer of a catheter balloon, comprising:
    a) wrapping a sheet of expanded polytetrafluoroethylene on a mandrel, the mandrel having a stainless steel or aluminum core and a thermoset polyimide jacket on an outer surface of the core, the thermoset polyimide jacket having an outer diameter and a length;
    b) heating the wrapped sheet of expanded polytetrafluoroethylene on the mandrel at a temperature of about 350° C. to about 390° C. to fuse sections of the wrapped sheet together to form an expanded polytetrafluoroethylene tube, without corroding the core of the mandrel and without changing the outer diameter and length of the polyimide jacket; and
    c) removing the expanded polytetrafluoroethylene tube from the stainless steel or aluminum core and the thermoset polyimide jacket of the mandrel, to form at least a layer of the catheter balloon.

12. The method of claim 11 wherein b) comprises heating the wrapped sheet for about 10 to about 30 minutes in an oven.

13. The method of claim 11 wherein the thermoset polyimide jacket has a thickness of about 0.025 to about 0.15 mm, and c) comprises removing the core of the mandrel from inside the expanded polytetrafluoroethylene tube and removing the polyimide jacket from inside the expanded polytetrafluoroethylene tube after the core of the mandrel is removed therefrom.

14. A method of making a tubular medical device or component, comprising:
   a) placing a sheet of a polymeric material on a mandrel, the mandrel having a metallic core and a jacket on an outer surface of the metallic core, the jacket having an outer diameter and a length and being formed of a polymeric material with a glass transition temperature of at least about 390° C. to about 420° C.;
   b) heating the sheet on the mandrel to an elevated temperature of about 350° C. to about 390° C. without changing the outer diameter and length of the jacket; and
   c) removing the heat treated polymeric material from the metallic core and the jacket of the mandrel.

15. The method of claim 14 wherein the polymeric material of the jacket is a thermoset polymeric material, and b) comprises heating the sheet for about 10 to about 30 minutes.

16. The method of claim 15 wherein the sheet of polymeric material is expanded polytetrafluoroethylene, and b) comprises heating the sheet at an elevated temperature of about 360° C. to about 380° C.

17. The method of claim 15 wherein b) comprises heating the sheet on the mandrel without corroding the metallic core of the mandrel.

* * * * *